United States Patent [19]

Paglione

[11] Patent Number: 5,051,921
[45] Date of Patent: Sep. 24, 1991

[54] METHOD AND APPARATUS FOR DETECTING LIQUID COMPOSITION AND ACTUAL LIQUID LEVEL

[75] Inventor: Robert W. Paglione, Mercer, N.J.

[73] Assignee: David Sarnoff Research Center, Inc., Princeton, N.J.

[21] Appl. No.: 443,527

[22] Filed: Nov. 30, 1989

[51] Int. Cl.⁵ .................. G01F 23/26; G01R 27/00
[52] U.S. Cl. .................. 364/509; 364/571.01; 73/1 H; 73/304 C; 340/618; 340/620; 331/65
[58] Field of Search .................. 364/509, 510, 571.01, 364/571.04; 73/1 H, 304 C, 304 R; 340/618, 620; 331/65

[56] References Cited

U.S. PATENT DOCUMENTS

| | | | |
|---|---|---|---|
| 3,768,006 | 10/1973 | Muellen | 324/61 |
| 3,774,237 | 10/1971 | Hardway, Jr. | 324/61 |
| 3,846,073 | 11/1974 | Baum | 23/230 A |
| 3,876,916 | 4/1975 | Stoakes | 317/249 R |
| 4,389,889 | 6/1983 | Larson | 73/304 C |
| 4,485,673 | 12/1984 | Stern | 364/509 |
| 4,545,020 | 10/1985 | Brasfield | 364/509 |
| 4,555,941 | 12/1985 | Fathauer et al. | 364/509 |
| 4,571,543 | 2/1986 | Raymond et al. | 324/425 |
| 4,589,077 | 5/1986 | Pope | 364/509 |
| 4,594,893 | 6/1986 | Lombard et al. | 73/304 C |
| 4,603,581 | 8/1986 | Yamanoue et al. | 73/304 C |
| 4,747,062 | 5/1988 | Esau | 364/509 |
| 4,799,174 | 1/1989 | Kramer et al. | 364/509 |
| 4,806,847 | 2/1989 | Atherton et al. | 324/61 P |
| 4,819,483 | 4/1989 | Emplit et al. | 364/509 |
| 4,977,528 | 12/1990 | Norris | 364/509 |

OTHER PUBLICATIONS

Suzuki, K. et al., "A Highly Accurate Fuel Level Measuring System", SAE Technical Paper Series 871961, Oct. 19, 1989.

Primary Examiner—Parshotam S. Lall
Assistant Examiner—Brian M. Mattson
Attorney, Agent, or Firm—W. J. Burke

[57] ABSTRACT

A liquid level and composition sensor includes a first interdigitated capacitor mounted substantially vertically in a tank, and a second interdigitated capacitor mounted substantially horizontally in and near the bottom of the tank. An electronic processor is responsive to the value of capacitance of the first capacitor for producing a first voltage signal proportional to the level of the liquid in the tank and is responsive to the value of capacitance of the second capacitor for producing a second voltage signal having a voltage level corresponding to the composition or dielectric constant of the liquid. The processor also multiplies the first and second voltage signals together to produce a liquid level voltage output signal having a constant slope for voltage amplitude versus liquid level, regardless of the composition of the liquid in the tank.

19 Claims, 5 Drawing Sheets

METHOD AND APPARATUS FOR DETECTING LIQUID COMPOSITION AND ACTUAL LIQUID LEVEL

FIELD OF THE INVENTION

The field of the present invention relates generally to liquid level and composition sensors.

BACKGROUND OF THE INVENTION

Many different types of level sensors are known for sensing the level of a liquid in a tank or other container. Such level sensors are employed for use in storage tanks, the fuel tanks for automotive vehicles, and so forth. The most common type of level sensor employs a float type mechanism, whereby the float rides upon the surface of the liquid being monitored and is connected via an arm to a transducer. Typically, the transducer is a variable resistor for providing a voltage or current signal that varies in amplitude in proportion to the level of the liquid being monitored. The level signal is applied to a meter for giving a visual indication of the level of fuel in the tank. Such meters are commonly known as fuel or gasoline gauges in automotive vehicle use and are mounted on the dashboard where they can be easily monitored by a driver.

During the fuel crisis experienced in the 1970's, alternative fuels were developed and sold in the marketplace. Such fuels included mixtures of gasoline and methanol or gasoline and ethanol, for example. It would be useful to a vehicle operator, or a mechanic, to have a sensor providing an indication of the composition of fuel being used in the vehicle at any given time. Also, and more importantly, such a sensor can provide the engine computer of the vehicle with fuel composition data to control engine performance. Such a sensor might give a readout of the percent gasoline or percent ethanol or percent methanol, for example. Also, because of the use of different mixtures of gasoline and other fuel products, the resultant mixtures provide dielectric values that are different for each mixture and different than that of pure gasoline. These dielectric differences will cause errors in the readout of the level of fuel in the tank in level sensing systems including either capacitive or inductive type transducers for detecting the level of fuel, calibrated for gasoline, for example.

A number of known systems for measuring and providing a visual or other indication of the level of fuel in a tank will now be discussed. Lombard et al., U.S. Pat. No. 4,594,893, discloses a capacitive probe for measuring the level of liquid in a tank or pipe. The probe includes, as shown in the Figures, particularly FIGS. 1, 2, and 3, rectangular strip-like sections upon which are formed metallic strips for providing a reference capacitor on the lowermost strip, which is always immersed in liquid in a tank for serving as a reference capacitor and for further providing two parallel measuring capacitors identical in length and capacitance on an upper rectangular strip portion of the device for measuring liquid level within the tank. The reference capacitor is connected in parallel with one of the upper measuring capacitors to provide in combination a reference capacitance for the device, whereas the other measuring capacitor provides for a detectable changing capacitance with different liquid levels for permitting sensing of the liquid level. Electronic circuitry 23 (see FIG. 2) is only shown as a reference numeral, but not described.

Raymond et al., U.S. Pat. No. 4,571,543, teaches the use of interdigitated capacitors for measuring the concentration of a specific non-aqueous gas. As shown in the figures, the interdigitated capacitors 11 and 31 are juxtaposed on a rectangular substrate, whereby through the use of appropriate coatings permeable only to the gas of interest, for example, relative to one of the interdigitated capacitors, to permit measurement of changes in the capacitance caused by the gas that are proportional to the concentration of the gas. The other interdigitated capacitor provides for temperature sensing, whereby the combination of the capacitances of the two capacitors at any given time permit the presence and concentration of a specific gas to be determined. Note in FIGS. 3 and 5 that the interdigitated capacitors are connected in a circuit including an oscillator and balanced diode-quad bridges. The output of the diode-quad bridges are passed through low pass filters, the output of the filter or filters is amplified, and the amplified signal is read out from a digital indicator 61 (see FIG. 3) for indicating the presence and concentration of the particular gas. Note in FIG. 5 that a microprocessor is used for scanning a plurality of interdigitated capacitors connected through associated balanced diode-quad bridges, low pass filters, and DC amplifiers.

Hardway, U.S. Pat. No. 3,774,237, teaches a method and apparatus for detecting the moisture content or ingredients ratio of a material by measuring the difference in dielectric constant between the material and a reference material through the use of capacitive probes placed in close proximity to the reference material and sample material, whereby the differences in capacitive coupling measured between the probes and the materials is used in an electronic sensing circuit to produce an electrical output signal proportional to the difference in the dielectric constants between the samples. The output signal, which is an alternating signal, is rectified and provided as a measurable direct current signal for indicating the moisture content or percentage of a particular ingredient in the material.

In Mueller, U.S. Pat. No. 3,768,006, a capacitive probe is used for providing a means for measuring the capacitance of an oil-water emulsion, whereby in conjunction with an electronic detection network, the capacitance value is compared with the capacitance of a known capacitor for obtaining a signal indicative of the difference in capacitance therebetween to determine the percent water in the oil-water emulsion. Note in FIG. 4, a curve is shown relating the dielectric of the oil-water emulsion/dielectric of oil to the percent water content in the emulsion. Other figures, such as FIG. 3, show the curves relating to the dielectric of the emulsion to the percent water content of the emulsion.

Baum et al., U.S. Pat. No. 3,846,073, teaches the use of a capacitive sensor for measuring the capacitance of a copolymer fluid and comparing the value of this capacitance to a reference value for determining the composition of the copolymer.

Stoakes, U.S. Pat. No. 3,876,916, discloses capacitive probes of a particular design and associated detection circuitry for measuring the capacitance of a circulating fluid. Electronic detection circuitry includes a capacitance bridge for detecting the capacitance and applying a signal across a meter calibrated to accurately read the value of the parameter being measured.

Larson, U.S. Pat. No. 4,389,889, teaches an apparatus for determining both the fuel level and the presence of water in the tank. Three individual plates are attached to the inside walls of the fuel tank. The plates are vertically oriented and juxtaposed to one another with the outer two of the plates being electrically connected together and the third plate located therebetween. An oscillator is connected to the two outermost plates for injecting an AC signal into the fluid in the tank. The signal from the oscillator is capacitively coupled to the center plate from the adjacent plates, and the level of the signal obtained from the center plate is detected, rectified, and supplied as a DC signal having an amplitude proportional to the level of the fluid to a meter 42 for providing a direct readout of the level. Also, another narrow strip-like plate 20 is located near the bottom of the tank, immediately below but separated from the previously mentioned center plate. The capacitance between the lowermost plate 20 and the center plate 14 is detected for determining when water is present in the tank. Since water is heavier than gasoline or diesel fuel, any water in the tank will drop to the bottom, and if sufficient in volume, will cover plate 20 causing a substantial increase in the signal level detected via plate 20, in turn causing a detection circuit to turn on a lamp indicating that the presence of water exceeds a predetermined level in the tank.

Yamanoue et al., U.S. Pat. No. 4,603,581, discloses a capacitive level sensing system for sensing the level of liquid in a vessel. In one embodiment, as shown in FIG. 8, Yamanoue teaches the use of a vertically oriented interdigitated capacitor across which a signal from an oscillator is connected, whereby the frequency of oscillation is determined by the value of capacitance measured, which is proportional to the level of fluid in the fuel tank. A sensing circuit for this configuration is not shown.

Atherton et al., U.S. Pat. No. 4,806,847, teaches the use of a capacitive probe for sensing the level of oil or transmission fluid in an engine. Signals developed across the probe and a reference capacitor are differentially detected with the detected output signal being rectified and provided as a signal proportional in level to the capacitance of the liquid or fluid being measured, which capacitance level is analogous to the level of the liquid.

SUMMARY OF THE INVENTION

An object of the invention is to provide an improved liquid level sensor.

Another object of the invention is to provide a system for sensing both the level and composition of liquid in a tank.

A further object of the invention is to provide a system for accurately indicating the level of liquid in a tank, regardless of the composition of the liquid within a range.

With the problems of the prior art in mind, in one embodiment of the invention, interdigitated capacitor means are included in a fuel tank for providing signals indicative of the level of fuel in the tank and the composition of the fuel in the tank. Electronic processing means are included for receiving the level and composition signals for providing an output signal indicative of the level of fuel in the tank regardless of the composition of the fuel and another output signal for indicating the composition of the fuel. The output signals are used to drive calibrated meters for indicating the percent ethanol or methanol in the gasoline contained in the tank, for example, and for indicating the level of fuel in the tank. Gain setting means are included in the electronic processor that is responsive to the level of the composition signal received from a transducer in the fuel tank for adjusting the amplitude of the level indicating output signal for accurately indicating on a level meter calibrated to the adjusted output signal range, for example, the level of fuel in the tank regardless of the composition thereof.

BRIEF DESCRIPTION OF THE DRAWINGS

Various embodiments of the present invention will be described below with reference to the figures of the drawings, in which like items are identified by the same reference designation, and in which.

DETAILED DESCRIPTION OF THE PREFERRED EMBODIMENTS OF THE INVENTION

Figure 1:
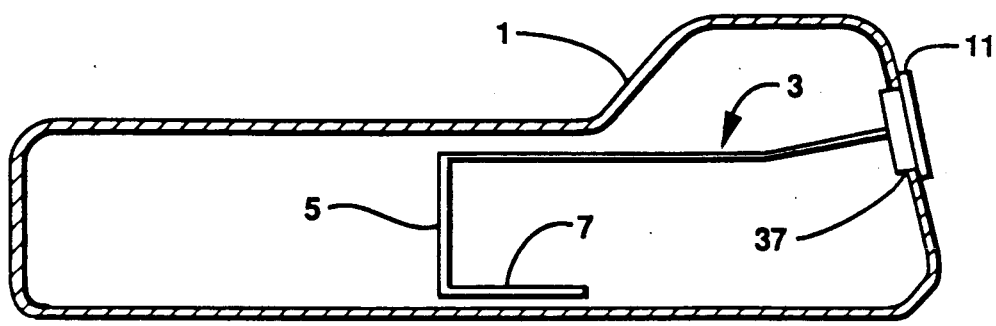
FIG. 1 shows a cross section of a fuel tank including a transducer and electronic assembly of one embodiment of the invention.
Figure 2:
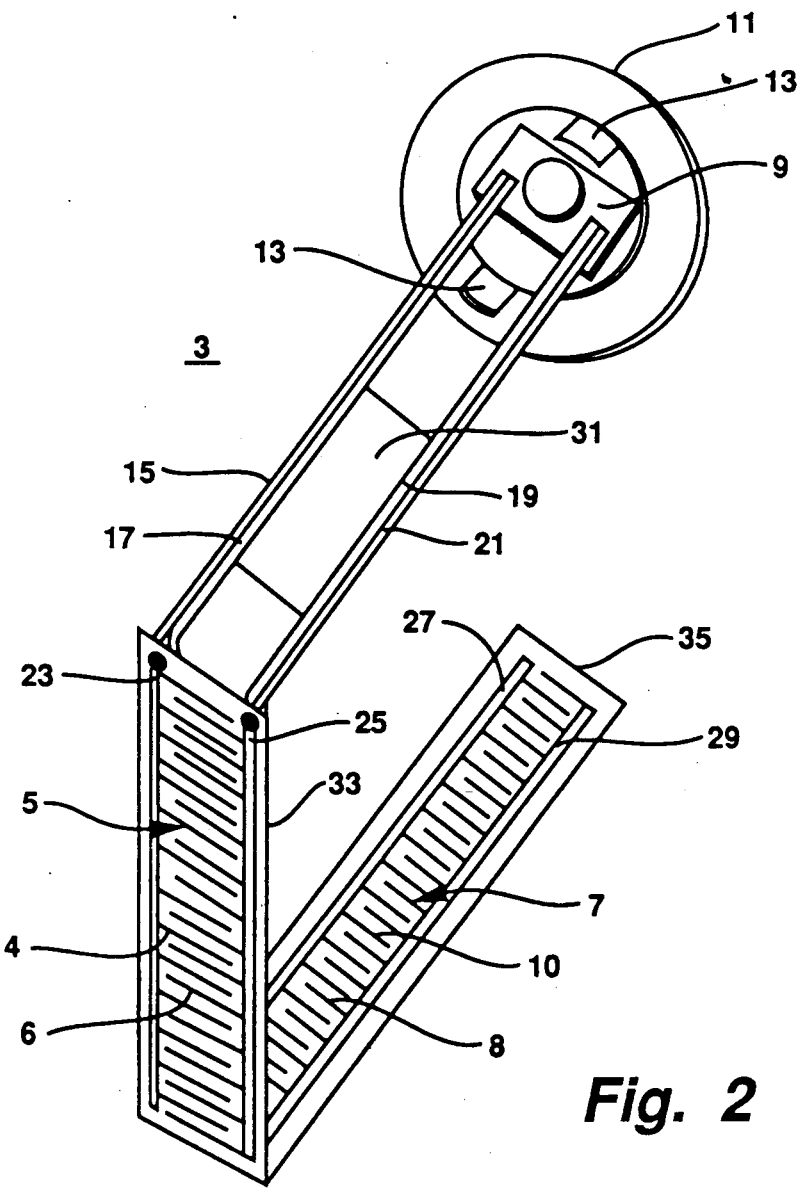
FIG. 2 shows a pictorial illustration of the transducer and electronic assembly of the embodiment of FIG. 1.

As shown in FIG. 1, a tank 1 for containing liquid includes a transducer and electronic module 3 with the latter being shown in greater detail in FIG. 2. The transducer portion of module 3 includes for placement in the tank, as shown, a vertically oriented interdigitated capacitor 5 and a horizontally oriented interdigitated capacitor 7, in this example. An electronic control module 9 is provided via an integrated circuit, for example. The electronic controller 9, in this example, is mounted in a cap-like member 11, as shown. The cap 11, which is circular in this example, includes two protruding mounting tabs 13 for permitting the cap 11 to be secured to the tank 1, as shown in FIG. 1. Appropriate gaskets, such as neoprene rubber seals, may be used to further seal the cap 11 with the attached interdigitated capacitors 5 and 7 to the tank 1.

As further shown in FIG. 2, the electronic module 9 is secured to the center portion of the cap 11. Four coaxial lines 15, 17, 19, and 21 are rigidly secured to the electronic module 9. In this embodiment, the coaxial lines 15, 17 are mounted on one side of the electronic module 9, and coaxial lines 19, 21 are mounted on the other or opposite side of electronic module 9, and are provided by small copper tubing. Insulated wires are run through the tubing for making appropriate electrical connections to the interdigitated capacitors 5 and 7. The insulated wire or conductor within tube 15 is connected at one end to one side 23 of the interdigitated capacitor 5 and at its other end to the electronic module 9. Another insulated wire within tubing 21 is connected between electronic module 9 and the other side 25 of interdigitated capacitor 5. A third insulated wire within tubing 17 is connected between the electronic module 9 and one side 27 of interdigitated capacitor 7. A fourth insulated wire within tubing 19 is connected between the electronic module 9 and the other side 29 of interdigitated capacitor 7. A separator plate 31 is secured between the tubing pair 15, 17, and the tubing pair 19, 21, via soldering, epoxying, or otherwise. Any materials used for any portion of the transducer and electronic module 3 must be impervious to the corrosive effects of any liquids, such as fuels that are expected to be placed in the tank 1. In a prototype for this embodiment of the invention, the interdigitated capacitors 5 and 7 were formed via copper printed circuits deposited on epoxy composition printed circuit boards or strips 33, 35, respectively. Any other suitable materials are applicable for use in this embodiment of the invention.

Note that in FIG. 1, the transducer and electronic module 3 is mounted via cap 11 through a hole 37 in the back wall of the tank 1, in this example. Other mounting configurations may also be used, one of which is described below for another embodiment of the invention. In the first described embodiment, the interdigitated capacitor 5 provides capacitance measurements for fuel level detecting, and the interdigitated capacitor 7 provides capacitance measurements for composition sensing. The two interdigitated capacitors 5 and 7 are shown in an "L"-shaped configuration, in this example, but in other applications, the capacitors 5 and 7 may be placed at other than 90° to one another.

Figure 3:
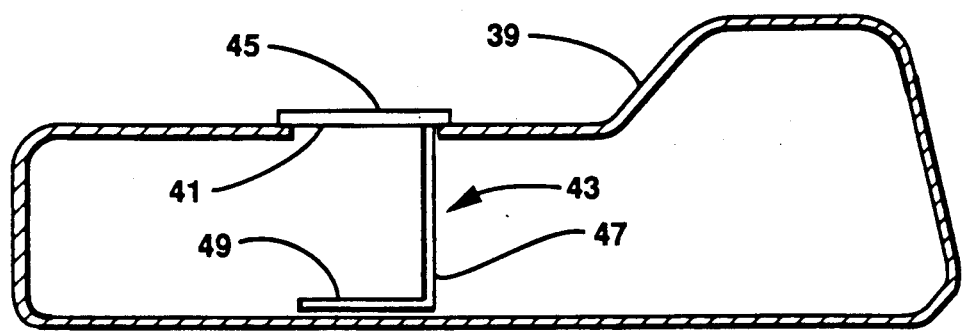
FIG. 3 shows a cross section of a fuel tank including a transducer and electronic assembly of another embodiment of the invention.
Figure 4:
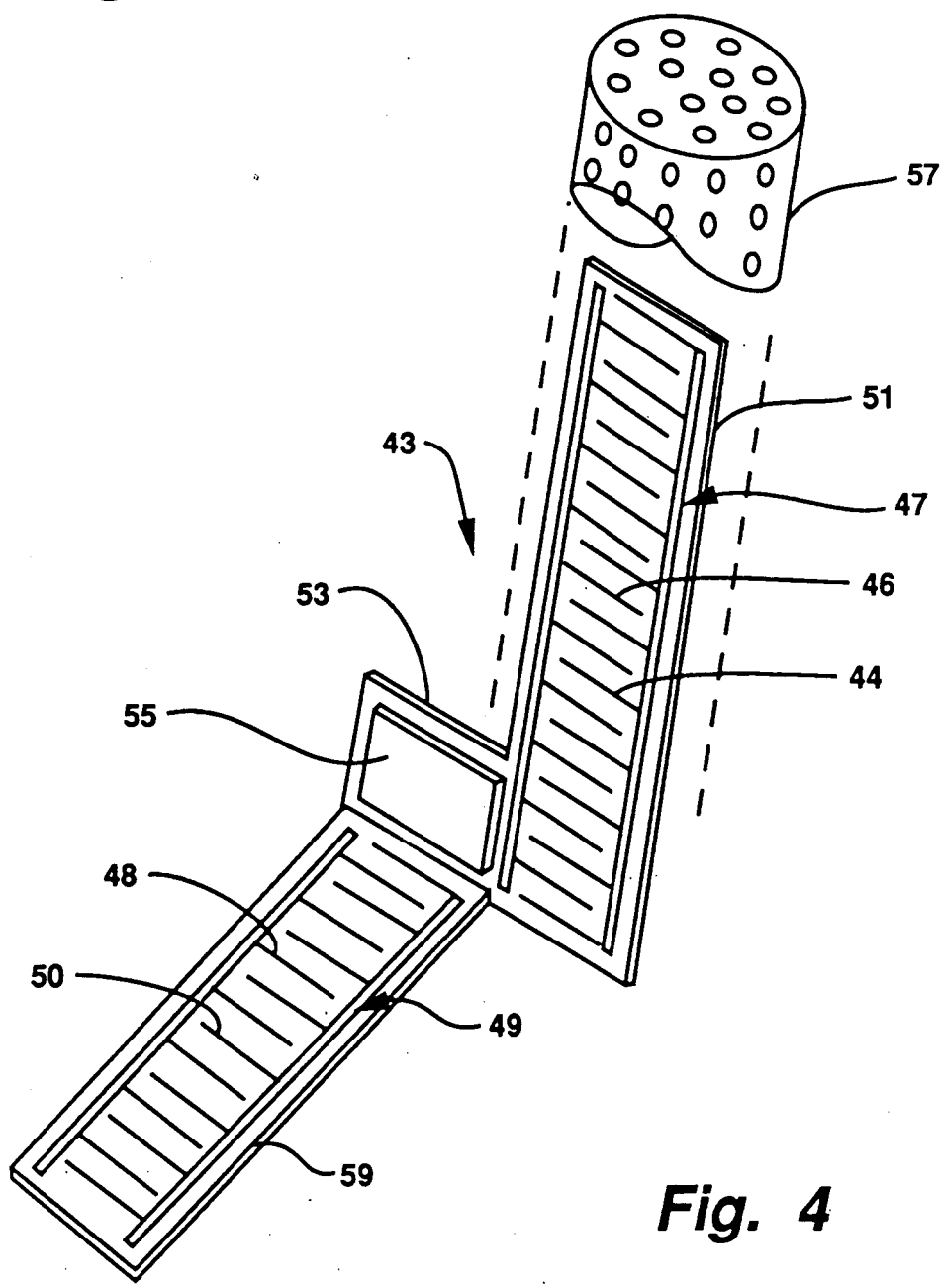
FIG. 4 shows a pictorial view of the transducer and electronic assembly of the embodiment of FIG. 3.

In FIG. 3, a fuel tank 39 includes a hole 41 for receiving a transducer and electronic module 43. The hole 41 is located in a central portion of the top frontal portion of the tank 39, in this example. The module 43 includes a mounting cap 45 for securing the module 43 to the tank 39 in a manner similar to that described for the embodiment of FIG. 1. With reference also to FIG. 4, the module 43 includes a vertically oriented interdigitated capacitor 47 for fuel level sensing and a horizontally oriented interdigitated capacitor 49 for fuel composition sensing. The interdigitated capacitors 47 and 49 are connected in an "L"-shaped configuration as shown. The printed circuit board 51 for the interdigitated capacitor 47 is itself "L"-shaped having a lower portion 53 upon which an integrated circuit 55 for the electronic processor of the module 43 is mounted as shown. In the embodiment of the invention of FIGS. 1 and 2, because of the long lead lengths between the capacitors 5 and 7 and the integrated circuit 9, the use of coaxial conductors 15, 17, 19, and 21 was required to insure accuracy of the detected capacitive measurements from the respective capacitors 5 and 7. In this second embodiment of FIGS. 3 and 4, the printed circuit lead lengths between the integrated circuit 55 and the capacitors 47 and 49 is relatively short. Accordingly, any capacitance or capacitive effects between the leads are substantially eliminated. In turn, this eliminates any requirement for coaxial shielding. Note that the coaxial tubing 15, 17, 19, and 21 of FIG. 2 is terminated to a source of reference potential, such as ground, in this example.

Sloshing of the fuel within the tank 39 may cause undesirable abrupt changes in the capacitance measurements from the capacitor 47. To dampen and substantially eliminate such perturbations in capacitance measurement, a perforated cylinder 57 of polypropylene, for example, can be mounted around capacitor 47 via conventional techniques, as shown. A similar perforated cylinder 57 can be placed or installed around capacitor 5 of the embodiment of FIGS. 1 and 2. Note that in FIG. 4 the printed circuit pads between the capacitors 47 and 49 to the integrated circuit controller 55 are not shown, but are included on the printed circuit boards 51, 53, and 59.

Figure 5:
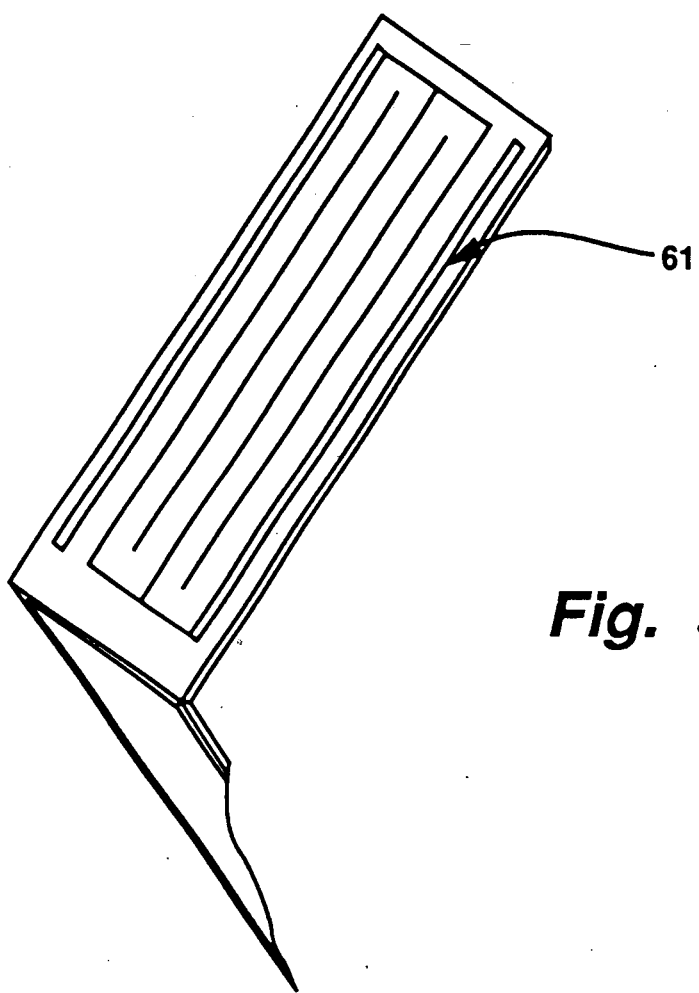
FIG. 5 is a partial pictorial view of a transducer assembly for an alternative embodiment of the invention.
Figure 6:
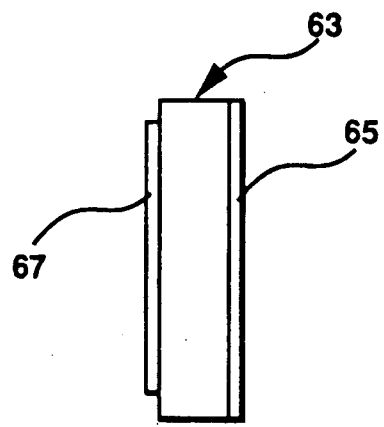
FIG. 6 is a top view of a typical transducer carrier or printed circuit board for various embodiments of the invention.

Other types of capacitive transducers than the interdigitated capacitor configurations 5, 7, of the two illustrated embodiments of the invention can be substituted therefor. For example, in FIG. 5 a printed circuit capacitor configuration 61 is shown that will provide linear changes in capacitance, with changes in liquid level, for example, rather than the step-like changes in capacitance provided by the previously described interdigitated capacitors, particularly 5 and 47. As shown in FIG. 6, the previously described capacitors 5, 7, 47, 49, and 61 can be provided via a printed circuit board 63 configuration having a ground plane 65 of copper, for example, deposited on one side, and the copper pattern 67 for the desired capacitor configuration printed on the other side of the board 63.

In engineering prototypes, the interdigitated capacitors 5, 7, 47, and 59 were made on rigid, 1/32 inch printed circuit boards 63 with a ground plane 65, as previously described. However, in testing of the engineering prototypes, it has been determined that the ground plane 65 is not necessary. Also, the use of a rigid printed circuit board 63 is not mandatory. Flexible circuits including Kapton, or Mylar, or Teflon (registered trademarks of E. I. DuPont Co., Wilmington, Delaware) can also be employed for the printed circuit substrate 63 in place of a rigid epoxy base board. Also, the electronic controllers 9 and 55, of the previously described embodiments, can be provided by a microprocessor or an imbedded type controller configuration, for example. The electronic controller configuration for one embodiment of the invention will be described in detail below. Also, the transducer and electronic control module 3 of the embodiment of FIGS. 1 and 2, and the similar module 43 of the embodiments of FIGS. 3 and 4, are conformably coated with a thin coating of a suitable material, such as Teflon (trademark of E. I. DuPont, Wilmington, DE), for protecting the components of the modules 3 and 43 from the corrosive effects of fuels that are placed in the associated tanks 1 and 39, respectively.

The spacing between the printed circuit lines 4 and 6 of capacitor 5, printed circuit lines 8 and 10 of capacitor 7, printed circuit lines 44 and 46 of capacitor 47, and printed circuit lines 48 and 50 of capacitor 49, directly affect the capacitance values measured from these capacitors at any given time. In an engineering prototype, these printed circuit lines were spaced 0.01 inch apart and were also 0.01 inch thick. In the embodiment of FIGS. 1 and 2 in the corresponding engineering prototype, the printed circuit board 33 for capacitor 5 was 5.75 inches long and 1 inch wide, whereas the printed circuit board 35 for capacitor 7 was made 3.5 inches long and 1 inch wide. For each one of the capacitors 5 and 7, the overlap between printed circuit lines 4 and 6, and printed circuit lines 8 and 10, respectively, was 0.5 inch. As a result, the measured capacitance of interdigitated capacitor 5 in air was 159.0 pf (picofarads) and of interdigitated capacitor 7 was 80.0 pf.

For purposes of illustration, the operation of the present invention and the description of the electronic controller will partly be made with reference to the embodiment of FIGS. 1 and 2. However, note that the embodiments of FIGS. 3, 4, and 5, for providing other capacitive transducers could just as well be utilized. Also, other than capacitive transducers may also be employed for obtaining the level and composition signals for processing in a manner similar to that described below.

In this example, assume that capacitor 7 is always immersed in fuel in tank 1. The measured value of capacitance of capacitor 7 when immersed, in fuel is proportional to the dielectric constant of the fuel mixture $\epsilon$ times the value of capacitance of capacitor 7 when in air. This relationship is expressed below in equation (1):

$$C_{7F} \approx \epsilon \cdot C_{7A} \quad (1)$$

Where $\epsilon$ = dielectric constant of the fluid in tank 1;
$C_{7A}$ = capacitance of capacitor 7 in air; and
$C_{7F}$ = capacitance of capacitor 7 in the fluid in tank 1.
To determine the composition of fuel or fluid in tank 1, equation 1 must be solved for the dielectric constant of the fluid at any given time. Note that $\epsilon$ of methanol is about 30, of ethanol is about 24, and of gasoline is about 2.

To determine the level of fuel or fluid in tank 1, through measurement of the value of capacitance of capacitor 5 at any given time, equation (2) as shown below must be solved for "H":

$$C_{5F} \approx C_{5A} + (C_{5A}/L)[H(\epsilon - 1)] \quad (2)$$

Where $C_{5F}$ = capacitance of capacitor 5 in fluid at a given time;
$C_{5A}$ = capacitance of capacitor 5 when totally in air;
L = total length of capacitor 5
and H = height of fluid in tank.
$C_{7A}$, $C_{5F}$, and L are parameters that can be easily measured, and therefore, are known. Accordingly, as previously mentioned, $\epsilon$ in equation "(1)" is solved for and substituted into equation "(2)" to solve for H. The electronic processor for providing such computations is described immediately below.

Figure 7:
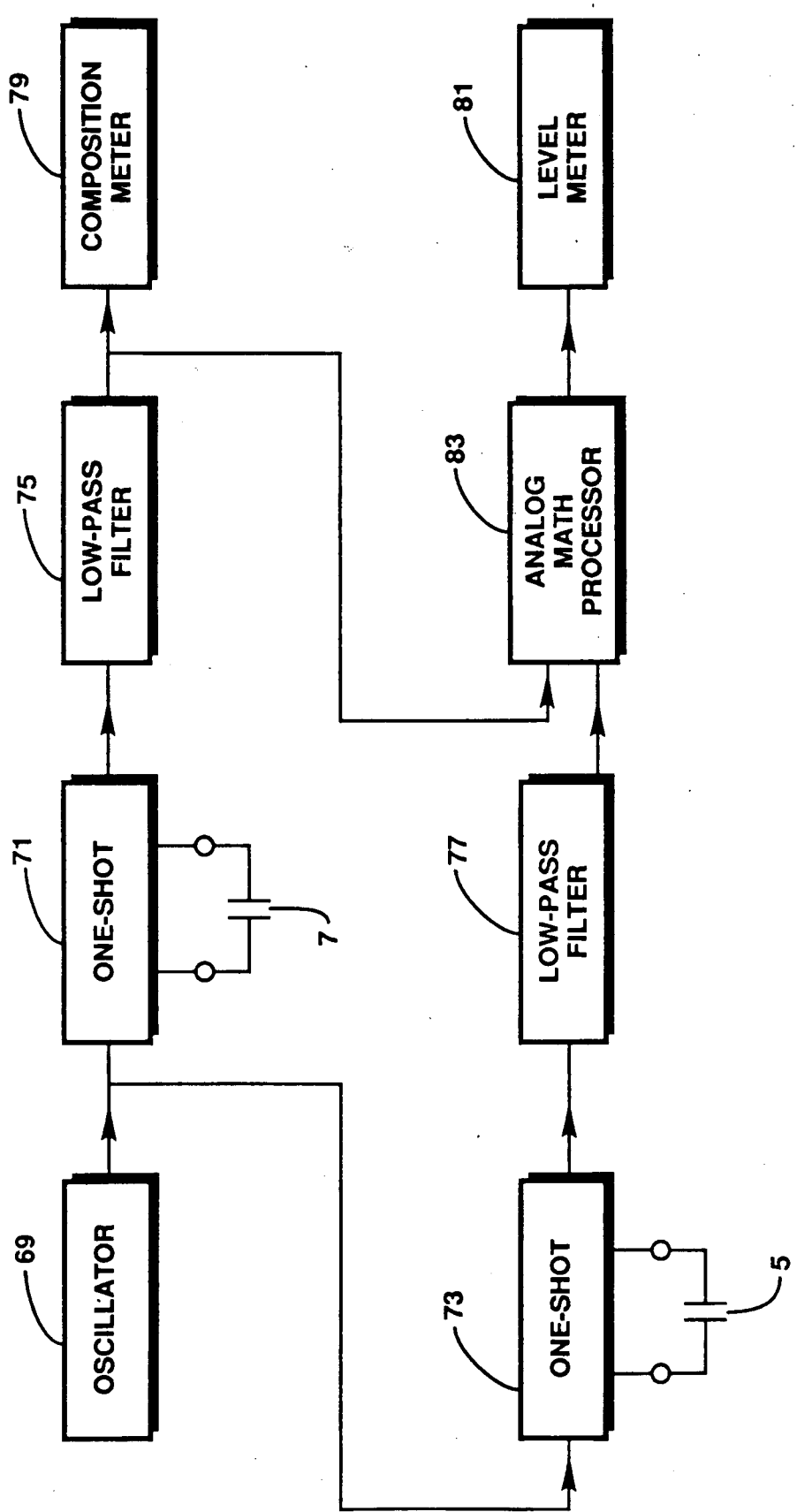
FIG. 7 is a block diagram of the electronic controller or processor for one embodiment of the invention.

In FIG. 7, a block diagram is shown of an electronic processor 83 for responding to the capacitance of capacitor 7 for providing an output signal indicative of the composition of fuel in tank 1 and responsive to the capacitance of capacitor 5 for providing an output signal indicative of the level of the fuel in tank 1. An oscillator 69 provides a pulse train of a given frequency and duty cycle for triggering two monostable multivibrators 71 and 73 (also known in the art as "one-shots"). The width or duration of the output pulses from one-shots 71 and 73 is directly proportional to the capacitance of capacitors 7 and 5, respectively. Also, the frequency of the output pulses from the one-shot 71 and 73 is determined by the frequency of the pulse train from oscillator 69. Low-pass filters 75 and 77 are responsive to the width of the output pulses from one-shots 71 and 73, respectively, for producing DC output voltages having levels that are proportional to such pulse widths, respectively. The output voltage from low-pass filter 75 has a level corresponding to the percent composition of ethanol or methanol to gasoline, for example, forming the fuel mixture in tank 1. In one embodiment of the invention, the voltage signal is applied to a composition meter 79 located on the dashboard of a vehicle, for example, calibrated for giving a visual readout of the percent composition of the fuel in the tank 1 at any given time. Meter 79 can be provided by an analog or digital voltmeter, for example.

Similarly, the level of the output voltage signal from the low-pass filter 77 is directly proportional to the level of liquid or fuel in the tank 1, regardless of the composition of the fuel. However, if this signal is directly applied to a level meter, such as level meter 81 calibrated for gasoline fuel only, not mixtures of gasoline and some other fluid, the indicated level or readout from meter 81 will only be accurate for pure gasoline. If mixtures of gasoline and ethanol or methanol, for example, are placed into tank 1, because of the change in the dielectric of the resulting mixture, the fuel level indicated by the meter 81 will be in error. The present inventor recognized this problem and developed a solution as shown in FIG. 7 by including an analog math processor 83 for processing the fuel composition voltage output signal from low-pass filter 75 and the fuel level output signal from low-pass filter 77 to produce an output voltage signal that has a unitary slope over a range of different levels of the fluid or fuel in tank 1, regardless of the composition of the fuel. A more detailed description of the electronic processor or control system follows. Note that the various embodiments of the invention are not limited to level sensing gasoline or mixtures of gasoline and ethanol or methanol but can be used for level sensing mixtures or pure amounts of any relatively non-conducting liquids.

Figure 8:
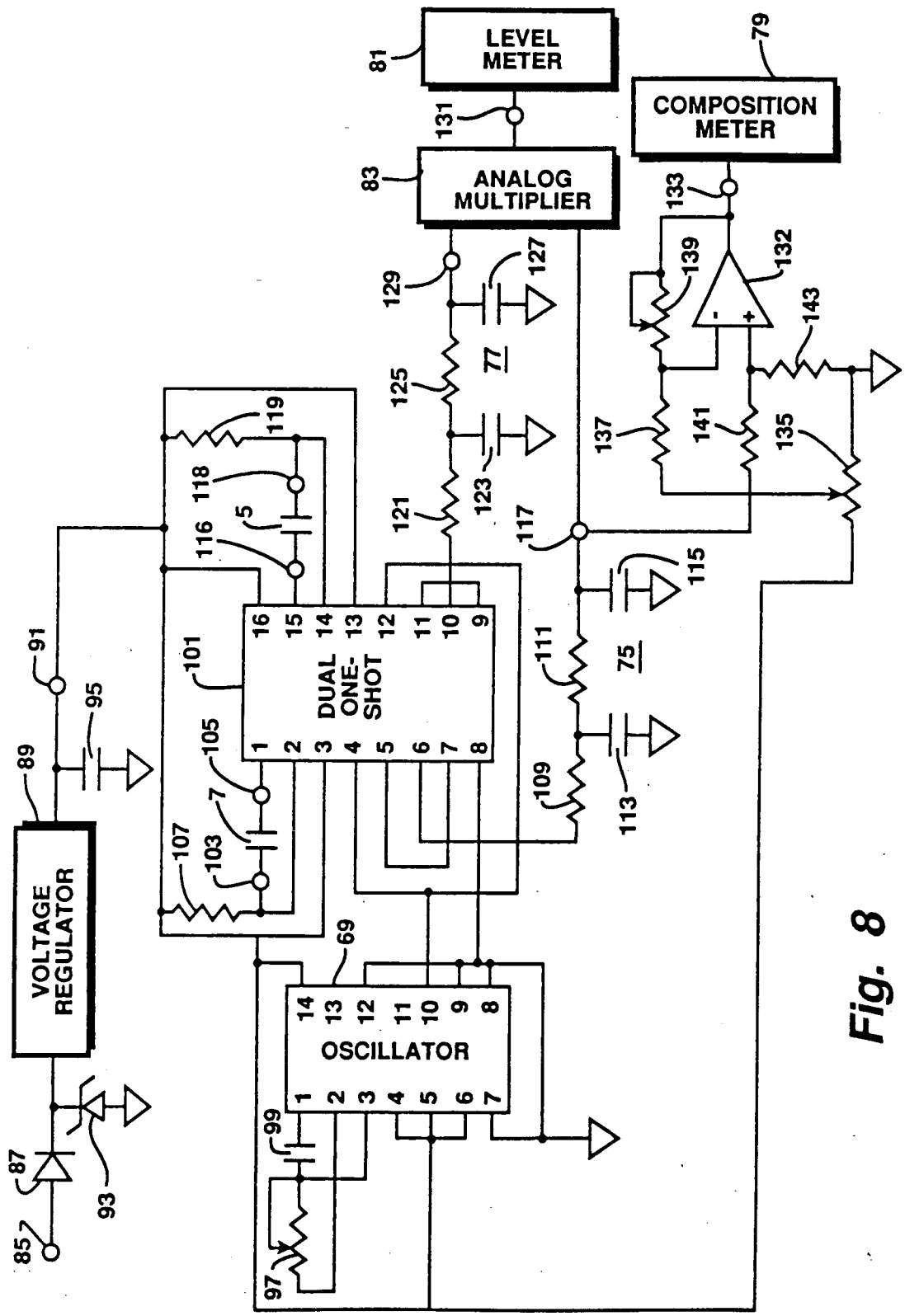
FIG. 8 is a block schematic diagram showing details of the electronic processor used in an engineering prototype for one embodiment of the invention.

In FIG. 8, a detailed block-schematic diagram is shown of an electronic processor used on an engineering prototype of the present invention for an automotive vehicle application. A voltage terminal 85 is connected to the battery of the vehicle, typically a 12 volt battery, whereby the voltage is connected via a blocking diode 87 to a voltage regulator 89. The voltage regulator 89 used on the engineering prototype was a 78L05 regulator manufactured by Motorola Inc., Phoenix, Arizona. The output voltage from the regulator 89 provides +5.0 volts DC at output voltage terminal 91 for providing power to the various active devices in the processor, as will be described. The blocking diode 87 is connected with its anode electrode to the battery voltage terminal 85 and its cathode electrode to the input of the voltage regulator 89 and to the cathode electrode of a zener diode 93. The anode electrode of zener diode 93 is connected to a source of reference potential, ground in this example. Blocking diode 87 prevents damage to the present processor 83 in the event of a reverse battery hookup thereto. Also, zener diode 93 is a 22.0 volt zener, and provides for over-voltage protection. A high-frequency by-pass capacitor 95 is connected between the output of voltage regulator 89 and ground, in this example.

The oscillator 69 is provided by a CD4047 integrated circuit oscillator produced by Harris Corporation, Somerville, New Jersey. As shown, the pin numbers for the particular oscillator 69 used in the engineering prototype are shown in FIG. 8, as are all connections thereto. Variable resistor 97 and capacitor 99 provide a tank circuit for oscillator 69 for determining the output frequency thereof. More specifically, the frequency of the output signal from oscillator 69 is determined from equation (3) below:

$$f = 1/(4.4RC) \quad (3)$$

Where f = frequency in Hz,
R = Resistance of resistor 97 in ohms,
C = capacitance of capacitor 99 in farads.

For the engineering prototype, potentiometer or variable resistor 97 was 25kΩ (25,000 ohms), and capacitor 99 was 120.0pf (picofarads). Accordingly, from equation 3, the frequency of oscillator 69 was equal to or greater than 76.0 kHz. The one-shots 71 and 73 were provided by a dual one-shot multivibrator integrated circuit part number CD4098 (Harris Corporation, Somerville, New Jersey). The combination of capacitor 7, that is of interdigitated capacitor 7 for providing a capacitance value equivalent to composition, is connected between terminals 103 and 105. The value of capacitor 7 in combination with the resistance of resistor 107 determines the width of the output pulse developed at pin "6" of one-shot 101 that is proportional to the composition of the fuel in tank 1. The low-pass filter 75 network includes resistors 109 and 111 and capacitors 113 and 115. As shown, one end of resistor 109 is connected to pin "6" of one-shot 101, and the other end is connected in common to one end of resistor 111 and one end of capacitor 113. The other end of resistor 111 is connected in common to one end of capacitor 115 and a voltage output or signal terminal 117. The other ends of capacitors 113 and 115 are connected to ground. The voltage developed at output terminal 117 has a voltage level corresponding to the dielectric constant or composition of the fuel in tank 1.

Capacitor 5 is connected via terminals 116 and 118 between pin "15" of one-shot 101 and the common connection of pin "14" of one-shot 101 and one end of resistor 119. The other end of resistor 119 is connected to voltage terminal 91.

The value of capacitance of interdigitated capacitor 5 at a given time, in combination with the resistance of resistor 119, determines the width of the output pulse produced at pin "10" of the dual one-shot 101. The output pulse width is directly proportional to the level of fuel in tank 1. This output pulse is passed to low-pass filter 77 including a resistor 121 having one end connected to pin "10" of one-shot 101 and another end connected in common to one end of a capacitor 123 and one end of another resistor 125. The other end of resistor 125 is connected in common to one end of a capacitor 127 and a voltage output or signal terminal 129. The other ends of capacitors 123 and 127 are connected to ground. The output voltage signal from low-pass filter 77 produced at terminal 129 has a voltage level that is proportional to the level of fuel in tank 1. The level voltage signal is applied to one input of the analog multiplier 83. The other input of the analog multiplier 83 is connected to voltage terminal 117 for receiving the composition voltage signal. In the engineering prototype, analog multiplier 83 was provided by a CA3091 multiplier (Harris Corporation, Somerville, New Jersey). Analog multiplier 83 operates to multiply together the composition voltage signal and level voltage signal for providing at output terminal 131 a fuel composition independent voltage level signal for providing a voltage level output signal that has the same voltage level for a particular level of fuel in tank 1, regardless of the composition of fuel in tank 1. In this manner, a voltage meter 81 can be calibrated to provide a visual indication of the level of fuel relative to the level of voltage of the voltage at terminal 131 independent of the composition of fuel in tank 1. In the engineering prototype, the value of resistors 107 and 119 were each 20.0kΩ, resistors 109, 111, 121, and 125 were each 10.0kΩ, and capacitors 113, 115, 123, and 127 were each 0.15 microfarads.

In the engineering prototype, the operational amplifier 132 processes the voltage signal developed at terminal 117 from low-pass filter 75, corresponding to the percent composition of the fluid in tank 1, to provide a composition voltage signal that ranges from 0 volt to 5.0 volts at terminal 133, to provide for easy calibration of the composition meter 79. A variable resistor 135 is connected with one end to terminal 91 for receiving +5.0 volts, in this example, and with its other end connected to ground. The arm of variable resistor 135 provides an adjustable bias voltage to one end of an input resistor 137, the other end of which is connected in common to the inverting terminal of operational amplifier 132, and to one end of another potentiometer of variable feedback resistor 139. The other end of variable resistor 139 is connected in common to the output of operational amplifier 132 and output terminal 133. Another input resistor 141 has one end connected to terminal 117 for receiving the composition signal from low-pass filter 75, and its other end connected in common to the noninverting terminal of operational amplifier 132, and one end of a pull-down resistor 143, the other end of the latter being connected to ground. Note that operational amplifier 132 was provided by an ALD1701 amplifier produced by Advanced Linear Devices, Inc., Sunnyvale, California.

In operation of the fuel level and composition sensor of FIG. 8, oscillator 69 is adjusted to provide a 100.0 kHz (kilohertz) pulse train with a 50% duty cycle. The prototype composition measuring transducer or capacitor 7, when in air, caused the dual one-shot 101 to produce a 3.0 microsecond pulse width signal at pin "6" thereof. Note that the capacitance of capacitor 7 in air was about 80.0pf, as previously mentioned. Similarly, the level detecting transducer or capacitor 5 with a measured capacitance in air of about 159.0pf caused a pulse having a width of about 6 microseconds to be produced at pin "10" of one-shot 101 with capacitor 5 in air. When capacitor 7 is in air, the level of the DC composition voltage signal appearing at terminal 117 is 1.65 volts. When capacitor 7 is emersed in 100% methanol, the voltage developed at terminal 117 is about +2.06 volts. With capacitor 7 in air, potentiometer 135 is adjusted to produce 0 volt DC at terminal 133. With capacitor 7 in methanol, potentiometer 139 is adjusted to provide +5.0 volts DC at terminal 133. In this manner the system is calibrated for providing a positive DC voltage signal at terminal 133 that at zero volts indicates 100% gasoline in tank 1, and at 5.0 volts indicates 100% methanol in the tank, in this example. The meter is calibrated in a linear manner between zero and 5.0 volts for providing a visual readout of the percent methanol in fuel tank 1 at any given time, for example. Alternatively, the meter can be provided with an indication of the percent gasoline, for example. In a similar manner, the system can be calibrated for ethanol or some other additive to gasoline.

As previously mentioned, the liquid or fuel level voltage signal from low-pass filter 77 produced at terminal 129 and the composition voltage signal from low-pass filter 75 produced at terminal 117 are multiplied together via analog multiplier 83 to produce a signal at terminal 131 that always represents the level of the fuel within tank 1, regardless of its composition. In other words, the composition voltage signal at terminal 117 is used to set the gain of the analog multiplier 83 for insuring that the level voltage signal at output terminal 131 is always representative of the level of the fuel in the tank, as calibrated. Level meter 81 is calibrated by plotting the level of the voltage at terminal 131 for different levels of fuel in tank 1.

Although various embodiments of the invention have been illustrated herein, they are not meant to be limiting, and variations to these embodiments may occur to those of skill in the art, which variations are meant to be covered by the spirit and scope of the claims appended hereto. For example, other than interdigitated capacitors 5 and 7 can be applied for use as the measuring transducers in the present system. Also, the electronic processor can be a digital system rather than the illustrated analog processor.

What I claim is:

1. A method for measuring a level of liquid in a tank having a top and a bottom and composition of the liquid, comprising the steps of:

generating a liquid level signal having a magnitude corresponding to the level of liquid in said tank;

generating a composition signal having a level corresponding to the dielectric constant of said liquid in said tank;

multiplying said liquid level signal and composition signals together for producing the product thereof as a true liquid level output signal having a level corresponding to the level of liquid in said tank regardless of the dielectric constant of said liquid; and calibrating a meter for receiving said true liquid level output signal and providing a visual readout of the level of liquid in said tank.

2. The method of claim 1, further including the step of calibrating a meter for receiving a calibration signal, and providing in response thereto a visual indication of the composition of said liquid.

3. A liquid level and composition sensor, for sensing and indicating a level of a liquid in a tank and composition of said liquid relative to its dielectric constant, comprising:

first transducer means mounted within said tank for producing a liquid level signal having a level corresponding to height of said liquid in said tank;

second transducer means mounted within said tank for producing a composition signal having a level corresponding to the dielectric constant of said liquid; and signal processing means responsive to said liquid level and composition signals for multiplying said signals together to produce an output level signal having a magnitude indicative of the actual level of liquid in said tank regardless of the composition of said liquid.

4. The sensor of claim 3, wherein said first transducer means includes a first interdigitated capacitor mounted substantially vertically in said tank, and said second transducer means includes a second interdigitated capacitor mounted substantially horizontally near the bottom of said tank.

5. The sensor of claim 3, further including meter means responsive to said output level signal for providing a direct visual readout of said liquid level.

6. The sensor of claim 3, further including meter means responsive to said composition signal for providing a direct visual readout of the composition of said liquid within a range.

7. The sensor of claim 3, wherein said first transducer means is a first capacitive transducer for providing a value of capacitance directly proportional to the level of liquid in said tank, said second transducer means is a second capacitive transducer for providing a value of capacitance directly proportional to the dielectric constant of said liquid at any given time, which is indicative of the composition of said liquid, and said signal processing means includes:

first means responsive to the value of capacitance of said first transducer means for producing a liquid level voltage signal having a voltage level directly proportional to the level of liquid in said tank;

second means responsive to the value of capacitance of said second transducer means for producing a composition voltage signal having a voltage level directly proportional to the dielectric constant of said liquid; and compensating means responsive to said composition voltage signal for changing the level of said liquid level voltage signal to correspond to a predetermined value of voltage indicative of a given level of liquid in said tank.

8. The sensor of claim 7 wherein said first means includes:

an oscillator for providing a driving signal;

a first monostable multivibrator connected to said first capacitive transducer and said oscillator for producing a train of output pulses having pulse widths proportional to the value of capacitance of said first capacitive transducer; and a first low-pass filter responsive to said output pulses from said first monostable multivibrator for producing said liquid level voltage signal.

9. The sensor of claim 8, wherein said second means includes:

a second monostable multivibrator connected to said second capacitive transducer and said oscillator for producing a train of output pulses having pulse widths proportional to the value of capacitance of said second capacitive transducer; and a second low-pass filter responsive to said output pulses from said second monostable multivibrator for producing said composition voltage signal.

10. The sensor of claim 9, wherein said compensating means includes an analog math processor for receiving and multiplying together said liquid level voltage signal and said compensation voltage signal, for producing a compensated liquid level voltage signal.

11. The sensor of claim 7, wherein said compensating means includes an analog math processor for receiving and multiplying together said liquid level voltage signal and said compensation voltage signal for producing a compensated liquid level voltage signal.

12. The sensor of claim 11, further including meter means responsive to said compensated liquid level signal for providing a visual indication of the level of liquid in said tank.

13. The sensor of claim 11, further including meter means responsive to said composition signal for providing a visual indication of the composition of liquid in said tank.

14. The sensor of claim 7, wherein said first capacitive transducer consists of an interdigitated capacitor arranged substantially vertically in said tank, and said second capacitive transducer consists of an interdigitated capacitor arranged substantially horizontally in said tank.

15. A sensor for sensing and indicating a level of fuel and its composition in a tank, wherein the composition of the fuel may vary, comprising:
- a first capacitive sensor mounted substantially vertically within said tank, the capacitance of said sensor corresponding to the level of fuel in said tank at any time;
- a second capacitive sensor mounted substantially horizontally near the bottom of said tank, so as to be immersed in fuel even at relatively low levels of fuel, the capacitance of said second sensor corresponding to the composition of said fuel; and
- electronic processing means responsive to the capacitances of said first and second sensors at any given time for producing a first output signal having over a range of different levels of fuel in said tank a uniform and constant slope of voltage level versus the level of fuel in said tank, regardless of the composition of the fuel within said tank, said electronic processing means including:
- monostable multivibrator means responsive to the capacitance of said first and second sensors for producing first and second output pulses having pulse widths proportional to the capacitance of said first and second sensors, respectively, at a given time;
- oscillator means for driving said multivibrator means to produce a train of said first and second pulses;
- pulse width-to-voltage conversion means for converting said trains of first and second pulses into first and second DC signals having voltage levels corresponding to the level and composition of fuel in said tank at any given time; and
- analog multiplier means for multiplying together said first and second DC signals, for producing a fuel level output signal having within a range the same DC voltage level for a given level of fuel in said tank regardless of the composition of fuel in said tank.

16. The sensor of claim 15, wherein said electronic processing means further includes:
- voltage level conversion means responsive to said second DC signal for producing a fuel composition output signal having a predetermined voltage level range over a range of different compositions of said fuel.

17. The sensor of claim 15 wherein said pulse width-to-voltage conversion means includes first and second low-pass filters for converting said first and second pulses into said first and second DC signals.

18. The sensor of claim 15, further including fuel level indicating means calibrated for receiving said fuel level output signal, and in response thereto providing a visual indication of the level of fuel in said tank.

19. The sensor of claim 16, further including fuel composition indicating means calibrated for receiving said fuel composition output signal, and in response thereto providing a visual indication of the composition of fuel in said tank.

* * * * *